US00PP10749P

United States Patent [19]

Hollabaugh

[11] Patent Number: Plant 10,749

[45] Date of Patent: Jan. 12, 1999

[54] PEACH TREE NAMED 'HB110'

[75] Inventor: Donald P. Hollabaugh, Biglerville, Pa.

[73] Assignee: Adams County Nursery, Inc., Aspers, Pa.

[21] Appl. No.: 893,719

[22] Filed: Jul. 11, 1997

[51] Int. Cl.[6] ..... A01H 5/00

[52] U.S. Cl. ..... Plt./43.2

[58] Field of Search ..... Plt./43.2, 42.1, Plt./43.3

[56] References Cited

U.S. PATENT DOCUMENTS

P.P. 8,558 1/1994 Reuter ..... Plt./43.2

*Primary Examiner*—Howard J. Locker
*Attorney, Agent, or Firm*—James A. Lucas

[57] ABSTRACT

A new and distinct variety of Peach tree, designated 'HB110', originated as a seedling in a block of 'Jerseyqueen'. It is a mid-season variety maturing after 'Loring' and before 'Cresthaven'. The fruit is yellow-fleshed, freestone, firm, large sized and flavorful. The surface of the fruit is attractively colored with a dark red blush over a rich golden background.

2 Drawing Sheets

BACKGROUND OF THE DISCLOSURE

This invention relates to Peach Trees and, more specifically, to peach trees referred to as a variety of *Prunus persica* Batsch.

I discovered this new and unique variety of peach tree as a seedling growing in a block of 'Jerseyqueen' (NJ216) in a cultivated area near Biglerville, Pa. Although it is not known for certain, it is believed that this new variety of peach tree is an open pollinated seedling of 'Jerseyqueen'. The tree of this invention produces a fruit of attractive commercial value, ripening eight days before 'Jerseyqueen'. This new variety of peach was asexualy reproduced by grafting near Aspers, Pennsylvania and such reproduction has shown this new variety to come true in successive generation. This propagation of the new variety by grafting under standard controlled conditions clearly discloses the continued maintenance of the characteristics described herein which distinguish this new variety from the parent variety and other related varietis of peach trees.

SUMMARY OF THE INVENTION

This new and distinctive variety of peach tree produces a large, yellow-fleshed fruit with an attractive red blush. it ripens after 'Loring' and before 'Cresthaven', two recognized standard, mid-season varieties in the Mid-Atlantic growing region. Fruit firmness and shipping quality are superior to other varieties ripening at the same time.

DESCRIPTION OF THE DRAWINGS

This new variety of peach tree is illustrated by the accompanying photographic drawings, depicting the plant by the best possible color representation using color photography.

BOTANICAL DESCRIPTION OF THE PLANT

Figure 1:
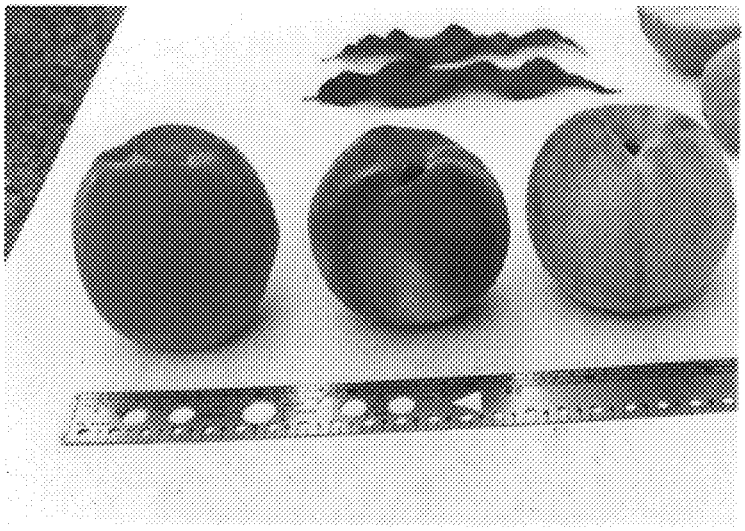
FIG. 1: Close-up of fruit from a four-year-old tree.
Figure 2:
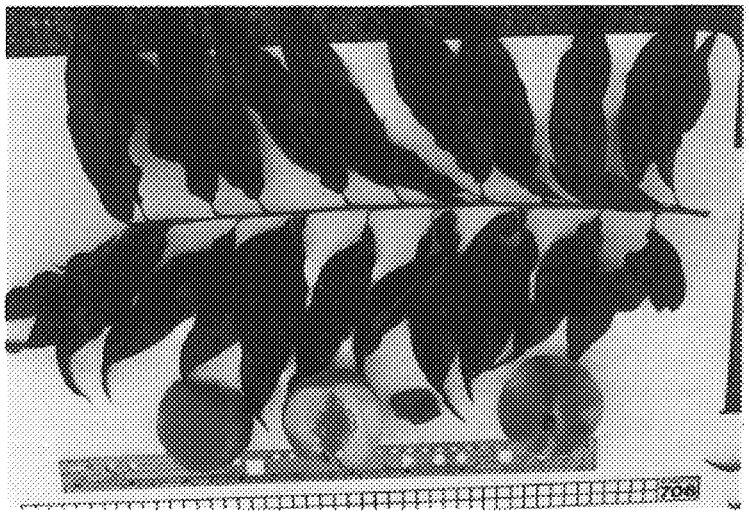
FIG. 2: Close-up of fruit, shoot and stone characteristics.
Figure 3:
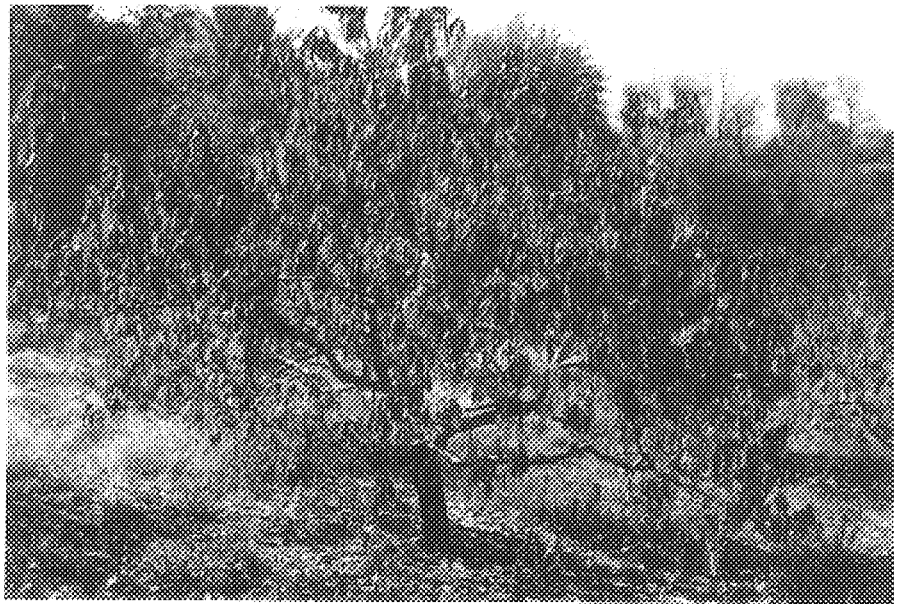
FIG. 3: Four-year-old tree.

All color references below are taken from The Royal Horticultural Society Colour Chart.

Parentage: Seedling.

*Female parent.*—*Prunus persica* 'Jerseyqueen'.

*Pollen parent.*—Unknown.

Asexually reproduced by bud grafting.

Tree: Medium-large size, vigorous, upright but not as much as 'Jerseyqueen', dense, vase formed, medium hardiness, productive on a good peach site, regular bearer.

*Trunk.*—Medium girth, medium smooth.

*Branches.*—Stocky, smooth, brown, dull. Lenticels: Numerous, small, inconspicuous.

*Leaves.*—Length — 6½ inches. Width — 1¾ inches. Medium sized, acuminate, acutely pointed, thin, smooth. Color — Medium green, 137C. Margins — Finely crenate. Petioles — Medium length, thick. Glands — Average number of 4 to 6, alternate, medium, reniform, green to brown, on stem and base of leaf.

*Flowers.*—Dates of first and full blossoms — April 10 and April 15, in Biglerville, Pa. (with 'Jerseyqueen'). Size — medium, showy. Bloom density — medium. Color — Rich pink, 65B.

*Fruit.*—Dates of first and last pickings — August 21 and 31 (for farm market). Maturity when described — Firm-ripe. Size — Large. Axial diameter — 3¼ inches. Transverse in suture plane — 9½ inches circumference. At right angles to suture plane — 9½ inches circumference. Form — Variable, unsymmetrical, globose. Suture — Shallow, has marked depression beyond pistil point. Ventral surface — Lips equal to unequal. Cavity — Elongated in suture plane with suture showing on both sides, depth ⅜ inch, breadth ½ inch, no markings. Base — Truncate. Apex — Rounded to truncate, depressed. Stem — Length ½ inch, medium, stout, medium adherence to stone. Skin — Medium thick, medium tender, free, no tendency to break. Color — Highly blushed (60 to 90% of surface) dark red, 60B, over yellow background, 23C. Down — Scant. Flesh — Yellow color, 20B. Surface of pit cavity — Red with yellow fibres. Texture — Fine, crisp. Fibers — Few, tender. Ripening — Even. Flavor — Mild. Aroma — Distinct. Eating quality — Best.

*Stone.*—Free, parts from flesh smoothly. Color — Burgundy, 59B. Fibers — Part from flesh smoothly. Size — Large. Length — 1¾ inch. Thickness — ¾ inch. Form — Oblong, cuneate toward base. Base — Oblique. Apex — Acuminate. Sides — Unequal, curved on right. Surface — Irregularly ridge pitted throughout. Ridges — Rounded toward apex. Pits — Angular. Dorsal edge — Deep, narrow grooves.

Uses: Local, dessert and culinary markets.

Keeping quality: Good.

Resistance to insects: Medium.

Resistance to disease: Medium, medium resistance to bacterial spot.

Shipping quality: Excellent.

I claim:

1. A new and distinct variety of Peach Tree, as illustrated and described, characterized by fruit of attractive color, firm flesh, excellent flavor, and excellent shipping quality.

* * * * *